United States Patent [19]  [11]  4,212,876
Houlihan  [45]  Jul. 15, 1980

[54] SUBSTITUTED OR UNSUBSTITUTED 2-PHENYLBENZIMIDAZOLES AS ANTI-OBESITY AGENTS

[75] Inventor: William J. Houlihan, Mt. Lakes, N.J.

[73] Assignee: Sandoz, Inc., E. Hanover, N.J.

[21] Appl. No.: 917,413

[22] Filed: Jun. 21, 1978

Related U.S. Application Data

[63] Continuation-in-part of Ser. No. 874,467, Feb. 2, 1978, abandoned, which is a continuation-in-part of Ser. No. 810,917, Jun. 29, 1977, abandoned.

[51] Int. Cl.² ........................................... A61K 31/415
[52] U.S. Cl. .................................................. 424/273 B
[58] Field of Search ..................................... 424/273 B

[56] References Cited

U.S. PATENT DOCUMENTS

| 3,080,282 | 3/1963 | Shunk | 424/273 |
| 3,778,504 | 12/1973 | Clemence et al. | 424/273 |

FOREIGN PATENT DOCUMENTS

| 263075 | 2/1964 | Australia | 424/273 |
| 1004073 | 9/1965 | United Kingdom | 424/273 |

Primary Examiner—Albert T. Meyers
Assistant Examiner—D. W. Robinson
Attorney, Agent, or Firm—Gerald D. Sharkin; Robert S. Honor; Timothy G. Rothwell

[57] ABSTRACT

Certain substituted or unsubstituted 2-phenylbenzimidazoles, e.g., 1-methyl-2-phenylbenzimidazole, are useful as anti-obesity agents.

7 Claims, No Drawings

SUBSTITUTED OR UNSUBSTITUTED 2-PHENYLBENZIMIDAZOLES AS ANTI-OBESITY AGENTS

This application is a continuation-in-part of copending application Ser. No. 874,467, filed Feb. 2, 1978, now abandoned which in turn is a continuation-in-part of Ser. No. 810,917, filed June 29, 1977 (now abandoned).

This invention relates to the pharmaceutical activity of substituted or unsubstituted 2-phenylbenzimidazoles. More particularly, this invention concerns the use of substituted or unsubstituted 2-phenylbenzimidazoles in the treatment of obesity. The invention also relates to pharmaceutical compositions containing these compounds as an active ingredient thereof.

The active agents with which this invention is concerned may be represented by the following structural formula:

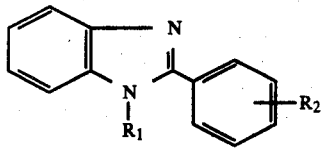

(I)

where $R_1$ represents lower alkyl, ie, alkyl having 1 to 4 carbon atoms, e.g., methyl, ethyl, isopropyl and the like, and $R_2$ represents hydrogen, fluoro or chloro.

The compounds of formula (I) above are known and may be prepared according to methods disclosed in the literature from known materials. The present invention contemplates only the novel use of such compounds as anti-obesity agents.

The compounds of formula (I) are useful because they possess pharmacological activity in animals. In particular, the compounds of formula (I) are useful as antiobesity agents in the treatment of obesity as indicated by (1) preventing an increase in the blood sugar level in male Wister rates in groups of 4 which have fasted for 16 hours and then are given an initial dose of 200 milligrams per kilogram of animal body weight of the test compound orally. One hour later, the rats are given 2 grams per kilogram of animal body weight of maltose load. Fifteen minutes after administration of the maltose, the rats are anesthetized with 120 milligrams per kilogram of animal body weight of sodium hexobarbital after which blood is collected via cardiac puncture. The blood samples are placed in an autoanalyzer cup containing 0.1 milliliters of heparin (1,000 units per milliliter). The heparinized blood is used to determine the blood sugar level with an autoanalyzer. The blood sugar content is compared to the control group which receives 0.5% carboxmethyl cellulose and are run concurrently, and by (2) preventing an increase in the blood sugar level in male Wistar rats in groups of 4 which are fasted for 16 hours and then are given an initial dose of 200 milligrams per kilogram of animal body weight of the test compound orally. One hour later, the rats are given 2.5 grams per kilogram of animal body weight of starch load. Thirty minutes after administration of the starch, the rats are anesthetized with 120 milligrams per kilogram of animal body weight of sodium hexobarbital after which blood is collected via cardiac puncture. The blood samples are placed in an autoanalyzer cup containing 0.1 milliliters of heparin (1,000 units per milliliter). The heparinized blood is used to determine the blood sugar level with an autoanalyzer. The blood sugar content is compared to the control group which receives 0.5% carboxymethyl cellulose and are run concurrently. The blood sugar levels are calculated and compared to the control.

For such use, the compounds of formula (I) may be administered orally or parenterally as such or admixed with conventional pharmaceutical carriers. They may be administered orally in such forms as tablets, dispersible powders, granules, capsules, syrups and elixirs, and parenterally as solutions, e.g., a sterile injectable aqueous solution. The compositions for oral use may contain one or more conventional adjuvants, such as sweetening agents, flavoring agents, coloring agents and preserving agents, in order to provide an elegant and palatable preparation. Tablets may contain the active ingredient in admixture with conventional pharmaceutically acceptable excipients, e.g., inert diluents, such as calcium carbonate, sodium carbonate, lactose, and talc, granulating and disintegrating agents, e.g., starch and alginic acid, binding agents, e.g., starch, gelatin and acacia, and lubricating agents, e.g., magnesium stearate, stearic acid and talc. The tablets may be uncoated or coated by known techniques to delay disintegration and absorption in the gastrointestinal tract and thereby provide a sustained action over a longer period. Similarly, suspensions, syrups and elixirs may contain the active ingredient in admixture with any of the conventional excipients utilized by the preparation of such compositions, e.g., suspending agents such as methylcellulose tragacanth and sodium alginate; wetting agents such as lecithin, polyoxyethylene stearate and polyoxyethylene sorbitan monooleate; and preservatives such as etyhl-p-hydroxybenzoate. Capsules may contain the active ingredient alone or admixed with an inert solid diluent, e.g., calcium carbonate, calcium phosphate and kaolin. The injectable compositions are formulated as known in the art. These pharmaceutical preparations may contain up to about 90% of the active ingredient in combination with the carrier or adjuvant.

Furthermore, the compounds of formula (I) may be similarly administered in the form of their non-toxic pharmaceutically acceptable acid addition salts. Such salts possess the same order of activity as the free base, are readily prepared by reacting the base with an appropriate acid, and, accordingly, are included within the scope of the invention. Representative of the acid addition salts are the neutral acid salts such as the hydrochloride, hydrobromide sulfate, phosphate and the like, and the organic salts such as succinate, benzoate, acetate, and the like.

The anti-obesity effective dosage of active ingredient employed for the treatment of obesity may vary depending on the particular compound employed, the mode of administration and the severity of the condition being treated. However, in general, satisfactory results are obtained for anti-obesity effect when the compounds of formula (I) are administered at a daily dosage of from about 1 milligram to about 400 milligrams per kilogram of animal body weight, p.o., preferably given in divided doses two to four times a day, or in sustained release form. For most large mammals, the total daily dosage for the anti-obesity indication is from about 25 to about 1000 milligrams. Dosage forms suitable for internal use comprise from about 6 to about 500 milligrams of the active compound in intimate admixture with a solid or liquid pharmaceutically acceptable carrier or diluent.

Compounds of formula (I) which can be used as the active ingredient include but are not limited to the following:

(a) 1-methyl-2-phenylbenzimidazole,
(b) 1-ethyl-2-phenylbenzimidazole,
(c) 1-butyl-2-phenylbenzimidazole, or
(d) 1-methyl-2-(p-fluorophenyl)-benzimidazole.

A representative formulation suitable for oral administration is a tablet or capsule prepared by standard tableting or encapsulating techniques which contains the following and may be administered 2 to 4 times a day in the treatment of obesity or diabetes:

| Ingredient | Weight (mg.) tablet | Weight (mg.) capsule |
|---|---|---|
| 1-methyl-2-phenylbenzimidazole | 100 | 100 |
| polyvinylpyrrolidone | 10 | — |
| lactose | 247.5 | 292 |
| corn starch | 25 | — |
| talcum | 15 | — |
| magnesium stearate | 2.5 | 8 |
| Total | 400 mg. | 400 mg. |

The following pharmaceutical compositions are formulated with the indicated amount of active agent using conventional techniques. The injectable suspension and the oral liquid suspension represent formulations useful as unit doses and may be administered in the treatment of obesity. The injectable suspension is suitable for administration once or twice a day whereas the oral liquid suspension is suitably administered 2 to 4 times per day for this purpose.

| Ingredient | sterile injectable suspension Weight (mg.) | oral liquid suspension Weight (mg.) |
|---|---|---|
| 1-methyl-2-phenylbenzimidazole | 200 | 100 |
| sodium carboxy methyl-cellulose U.S.P. | 5 | 12.5 |
| methyl cellulose | — | — |
| polyvinylpyrrolidone | — | — |
| lecithin | — | — |
| benzyl alcohol | 0.01 | — |
| magnesium aluminum silicate | — | 47.5 |
| flavor | — | q.s. |

-continued

| Ingredient | sterile injectable suspension Weight (mg.) | oral liquid suspension Weight (mg.) |
|---|---|---|
| color | — | q.s. |
| methyl paraben, U.S.P. | — | 4.5 |
| propyl paraben, U.S.P. | — | 1.0 |
| polysorbate 80 (e.g., Tween 80), U.S.P. | — | 5 |
| sorbitol solution, 70%, U.S.P. | — | 2,500 |
| buffer agent to adjusted pH for desired stability | q.s. | q.s. |
| water | q.s. for injection, q.s. to 1 ml. | q.s. to 5 ml. |

The preferred pharmaceutical compositions from the standpoint of preparation and ease of administration are solid compositions, particularly hard-filled capsules and tablets containing from about 100 to 200 milligrams of the active ingredient.

What is claimed is:

1. A method for treating obesity by preventing the absorption of glucose which comprises administering orally or parentally to a mammal in need of said treatment a weight reducing amount of a compound of the formula

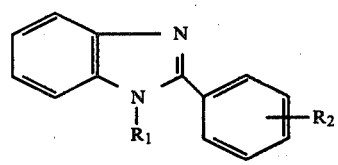

wherein
$R_1$ represents lower alkyl having 1 to 4 carbon atoms, and
$R_2$ represents hydrogen, fluoro or chloro.

2. The method of claim 1 in which the compound is 1-methyl-2-phenylbenzimidazole.

3. The method of claim 1 in which the compound is 1-ethyl-2-phenylbenzimidazole.

4. The method of claim 1 in which the compound is 1-butyl-2-phenylbenzimidazole.

5. The method of claim 1 in which the compound is 1-methyl-2-(p-fluorophenyl)-benzimidazole.

6. The method of claim 1 wherein the compound is administered orally at a daily dosage of from about 25 milligrams to about 1000 milligrams.

7. The method of claim 1 wherein the compound is orally administered in a unit dosage form comprising from about 6 milligrams to about 500 milligrams per unit dosage.